United States Patent [19]

Mahurkar

[11] Patent Number: 4,583,968
[45] Date of Patent: Apr. 22, 1986

[54] SMOOTH BORE DOUBLE LUMEN CATHETER

[76] Inventor: Sakharam D. Mahurkar, 6171 N. Sheridan, Suite 1112, Chicago, Ill. 60660

[21] Appl. No.: 641,187

[22] Filed: Aug. 15, 1984

Related U.S. Application Data

[63] Continuation of Ser. No. 538,671, Oct. 3, 1983.

[51] Int. Cl.⁴ .............................................. A61M 5/00
[52] U.S. Cl. ....................................... 604/43; 604/280
[58] Field of Search ............................ 604/43–45, 604/280

[56] References Cited

U.S. PATENT DOCUMENTS

| D. 250,349 | 11/1978 | McFarlane | D24/54 |
|---|---|---|---|
| D. 256,617 | 8/1980 | Clemens | D24/54 |
| D. 272,651 | 2/1984 | Mahurkar | . |
| 998,339 | 7/1911 | Hollins | 27/24 A |
| 1,290,647 | 1/1919 | Nyvall | 128/214 R X |
| 2,175,726 | 10/1939 | Gebauer | 128/349 B |
| 2,474,665 | 6/1949 | Guarino | 128/DIG. 3 |
| 2,564,977 | 8/1951 | Hsi Hu | 128/221 X |
| 2,590,895 | 4/1952 | Scarpellino | 128/221 |
| 2,625,932 | 1/1953 | Salisbury | 128/214.2 |
| 3,324,853 | 6/1967 | Czorny et al. | 128/214.4 |
| 3,463,152 | 8/1969 | Sorenson | 128/214.4 |
| 3,550,591 | 12/1970 | MacGregor | 128/214.4 |
| 3,804,097 | 4/1974 | Rudie | 128/350 R |
| 4,027,668 | 6/1977 | Dunn | 128/214 R |
| 4,096,860 | 6/1978 | McLaughlin | 128/214.4 |
| 4,098,275 | 7/1978 | Consalvo | 128/221 X |
| 4,099,528 | 7/1978 | Sorenson et al. | 128/214.4 |
| 4,134,402 | 1/1979 | Mahurkar | 128/221 X |
| 4,144,884 | 3/1979 | Tersteegen et al. | 128/214.4 |
| 4,180,068 | 12/1979 | Jacobsen et al. | 128/214 R |
| 4,202,332 | 5/1980 | Tersteegen et al. | 128/221 X |
| 4,203,436 | 5/1980 | Grimsrud | 128/214 R |
| 4,270,535 | 7/1981 | Bogue et al. | 128/214.4 |
| 4,336,036 | 6/1982 | Leeke et al. | 128/214 R X |
| 4,385,631 | 5/1983 | Uthmann | 604/284 |
| 4,403,983 | 3/1983 | Edelman et al. | 604/43 |
| 4,451,252 | 5/1984 | Martin | 604/43 |
| 4,493,696 | 1/1985 | Uldall | 604/43 |

FOREIGN PATENT DOCUMENTS

| 834211 | 2/1976 | Belgium | 128/221 |
|---|---|---|---|
| 1092927 | 1/1981 | Canada | 604/43 |
| 50089 | 8/1982 | Canada | . |
| 36642 | 9/1981 | European Pat. Off. | 604/43 |
| 2259865 | 6/1974 | Fed. Rep. of Germany | 128/221 |
| MR19346 | 6/1982 | Fed. Rep. of Germany | . |
| 592193 | 4/1925 | France | 128/214.2 |
| 821344 | 4/1982 | France | . |
| 55-88771 | 7/1980 | Japan | 128/348 |
| 1419702 | 12/1975 | United Kingdom | 128/221 |
| 1006219 | 3/1983 | United Kingdom | . |

OTHER PUBLICATIONS

McIntosh et al., "Double Lumen Catheter," *J.A.M.A.*, Feb. 21, 1959, pp. 137/835–138/836.

*Dorland's Illustrated Medical Dictionary*, 25th Ed., W. B. Saunders Co., Philadelphia, 1974, p. 274.

Brenner & Rector, *The Kidney*, vol. III, W. B. Saunders Co., Philadelphia, 1976, p. 164.

Tohoku, J., "Single Two-Lumen Cannula Dialysis", Aug., 1974.

ASAIO Abstracts, vol. 5, 22nd Annual Meeting, San Francisco Calif., Apr. 1-3, 1976, p. 52.

*Primary Examiner*—Dalton L. Truluck
*Attorney, Agent, or Firm*—Leydig, Voit & Mayer, Ltd.

[57] ABSTRACT

A double-current catheter having an elongated cylindrical tube for injection and removal of fluid is provided with a smooth conical tapered tip that smoothly merges with the cylindrical surface of the tube so that insertion trauma and the possibility of kinking are minimized. To provide improved dilator characteristics, preferably the tip includes a relative concentration of material for rigidity, the conical taper is gradual and the apex of the conical tip is substantially centered on the axis of the cylindrical tube. To promote fluid flow, the cylindrical tube preferably includes an internal planar divider defining two "D" shaped lumens. A first lumen extends from the proximal end of the cylindrical tube to a first opening at the distal end, and the second lumen extends from the proximal end to a side opening in the cylindrical surface of the tube. Preferably additional side holes for the lumens are provided to enhance fluid flow.

25 Claims, 7 Drawing Figures

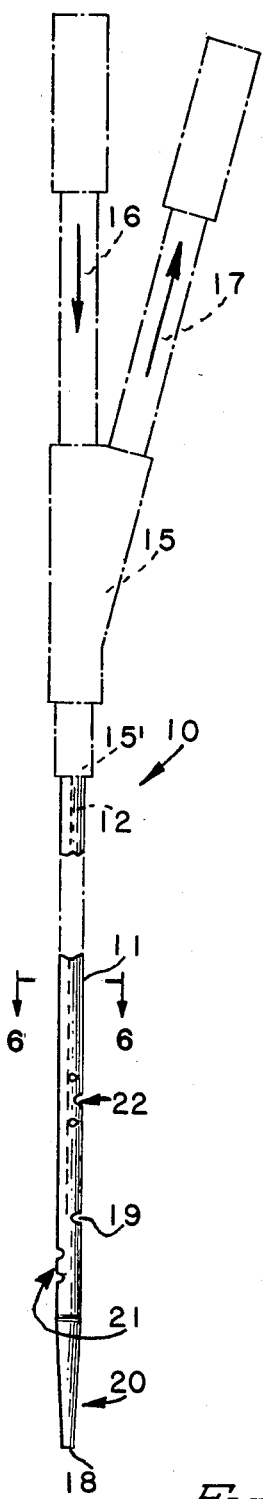
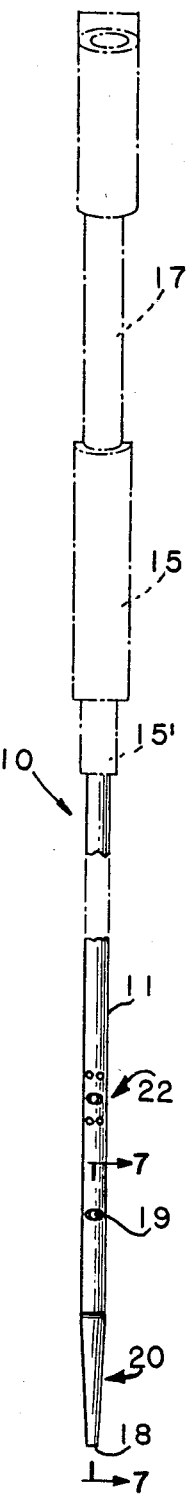
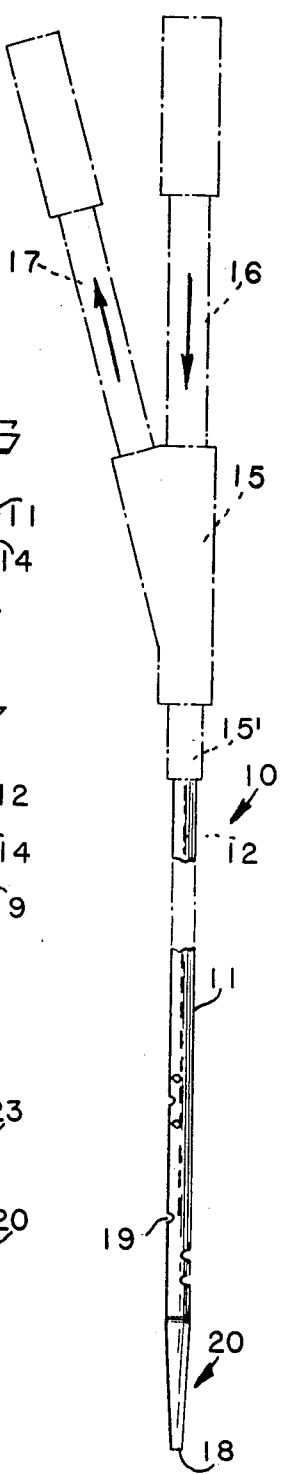
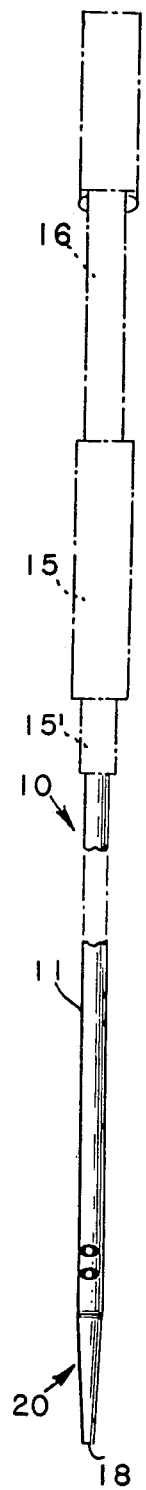
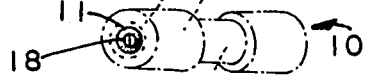

SMOOTH BORE DOUBLE LUMEN CATHETER

RELATED APPLICATIONS

The present application is a continuing application of Ser. No. 538,671 filed Oct. 3, 1983.

BACKGROUND OF THE INVENTION

1. Field of the Invention

The present invention relates to surgical instruments for withdrawing fluids from or introducing fluids into a cavity of the body.

2. Description of the Related Art

As is well known, a catheter is a tubular, flexible, surgical instrument for withdrawing fluids from (or introducing fluids into) a cavity of the body. A double-current catheter is a catheter having two channels; one for injection and one for removal of fluid. *Dorlan's Illustrated Medical Dictionary Twenty-Fifth Edition* (W. B. Saunders, Philadelphia 1974), p. 274. As is well known, a double-current catheter is used for removing blood from a fistula or vein for processing in a dialysis machine and returning the processed blood back to the fistula or vein. A double-current catheter suitable for this purpose is disclosed in Mahurkar, U.S. Pat. No. 4,134,402 issued Jan. 16, 1979. Mahurkar U.S. Pat. No. 4,134,402 discloses a double lumen continuous flow hemodialysis needle and cannula having contiguous lumens of different lengths formed by dividing a unitary straight tube, the shorter lumen acting as a blood intake lumen and the longer acting as a blood return lumen. Semi-circular lumens provide a minimal resistance to blood flow resulting in a smaller but highly efficient catheter in comparison to a coaxial double-current catheter. Hemodialysis requires, for example, a blood flow rate of about 200 ml/min or more and flow resistance less than about 100 mm of mercury.

There are numerous other United States Patents disclosing double-current catheters for hemodialysis and evidencing a long-felt need for a small, functionally efficient catheter having a minimum of insertion trauma and potential for clotting. McLaughlin, U.S. Pat. No. 4,096,860 issued June 27, 1978 discloses a coaxial hemodialysis catheter said to allow a step enlargement of the opening of a blood vessel to avoid tearing and rupture of the side walls. A simultaneous flow device incorporates a hub with an extension conduit and a valve therein for receipt of a needle therethrough. The extension conduit is of sufficient size to allow the passage of the needle therethrough adjacent the interior side walls thereof with an attendent extension thereof from its opening. The needle with the extension conduit is adapted for combined insertion within a blood vessel, after which it can be withdrawn while the valve prevents the backflow of blood through the axial passage of the hub. A coaxial flow device can then be inserted within the hub conduit.

Sorenson et al., U.S. Pat. No. 4,099,528 issued July 11, 1978 discloses a coaxial double lumen cannula mounted upon a hub and having a central stylet needle for penetrating a patient's vein and which is retractable after penetration.

Grimsrud, U.S. Pat. No. 4,203,436 issued May 20, 1980 discloses a hollow hypodermic needle with a divider for providing a first channel for removal of blood for treatment from a punctured blood vessel and a second channel for returning the treated blood to the blood vessel.

Uthmann, U.S. Pat. No. 4,385,631 issued May 31, 1983 discloses a hemodialysis catheter for puncturing blood vessels which includes a section insertable through a puncture opening into a blood vessel and a hose line following thereafter.

Jacobson et al., U.S. Pat. No. 4,180,068 issued Dec. 25, 1979 discloses a double-current hemodialysis catheter comprising a primary tube and an internal divider which also functions as a trocar and valve. The primary tube has a side opening for receiving blood and a central opening at the distal end of the primary tube. The internal divider includes a cutting end which protrudes from the distal opening when the divider is longitudinally moved to an insert position. In the insert position, blood flow is blocked.

Mahurkar, U.S. Pat. No. Des. 272,651 issued Feb. 14, 1984 discloses a double lumen catheter having an outlet lumen which has an opening at the tip of the catheter and a shorter inlet lumen which terminates in a bevel substantially displaced from the tip.

SUMMARY OF THE INVENTION

The primary object of the invention is to provide an efficient dual lumen catheter having minimal insertion trauma and a minimal potential for clotting.

Another object of the invention is to provide a dual lumen catheter which is an effective dilator for soft tissue and veins.

In accordance with the invention, a dual lumen catheter has a smooth conical tapered tip that smoothly merges with the catheter body so that insertion of the catheter is facilitated. The tip guidance point is located at the center of the conical tip for uniform distribution of frictional resistance and minimization of insertion trauma and kinking. The conical tapered tip comprises a relative concentration of material to impart relative rigidity so that the tip functions as an effective dilator for soft tissue and veins. Semicircular lumens insure non-static laminar flow and prevent clotting. The smooth bore double lumen catheter is particularly advantageous when a tunneling procedure or blind technique must be used, for example, to reach a vein under the collar bone or neck.

BRIEF DESCRIPTION OF THE DRAWINGS

Other objects and advantages of the invention will become apparent from the following detailed description and the accompanying drawings, in which:

FIG. 1 is a front elevational view of a smooth bore double lumen catheter according to the present invention;

FIG. 2 is a right side elevational view of the smooth bore double lumen catheter illustrated in FIG. 1;

FIG. 3 is a rear elevational view of the smooth bore double lumen catheter illustrated in FIG. 1;

FIG. 4 is a left side elevational view of the smooth bore double lumen catheter illustrated in FIG. 1;

FIG. 5 is a bottom view of the smooth bore double lumen catheter illustrated in FIG. 1;

FIG. 6 is a view in section of the smooth bore double lumen catheter illustrated in FIG. 1 taken along line 6—6 thereof; and FIG. 7 is a view in section of the smooth bore double lumen catheter illustrated in FIG. 1 taken along long 7—7 shown in FIG. 2.

While the invention will be described in connection with a certain preferred embodiment, it will be understood that it is not intended to limit the invention to that particular embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

Turning now to the drawings, FIGS. 1-5 show the various external views of a smooth bore double lumen catheter, generally designated 10, in accordance with the present invention. As is conventional for a double-current catheter, the double lumen catheter 10 has a elongated hollow tube 11 which is inserted into a cavity of the body such as a fistula or vein. The tube 11 is circular in cross section, as specifically shown in FIG. 6, and has an internal divider 12 defining a return lumen 13 and an inlet lumen 14 within the interior of the hollow tube 11. The lumens 13 and 14 are semicircular or "D" shaped which minimizes resistance to fluid flow. As is conventional for this type of dual lumen construction, the divider 12 extends axially along the tube 11 from a branching connector 15. The branching connector 15 connects the distal end portions of the return lumen 13 and the inlet lumen 14 to respective fluid return and inlet lines 16 and 17 which are, for example, respective venous and arterial lines of a dialysis circuit. This preferred direction of fluid circulation is indicated by heavy arrows in FIGS. 1 and 3. The branching connector 15 includes a coaxial sleeve 15' at the junction of the tube 11 and the connector 15. The sleeve 15' acts as a strain relief and also prevents kinking of the tube 11 at the junction.

The hollow tube 11 includes openings or apertures at the distal end portions of the lumens 13, 14 to permit the flow of fluid between a body cavity (not shown) and the lumens. The return lumen 13 extends along the entire length of the tube 11 to an aperture or opening 18 at the distal end or tip of the tube 11 as is more clearly shown in FIG. 7. The inlet lumen 14 is shorter than the return lumen 13 and terminates at its distal end at an aperture or opening 19 that is in the side of the tube 11 and is substantially displaced from the aperture 18 at the distal end of the tube 11.

In accordance with the invention, the distal end portion of the tube 11 has a conical tip generally designated 20 which smoothly merges with the cylindrical body of the tube 11. Preferably the apex of the conical tip 20 is centered on the axis of the cylindrical body of the tube 11 thus serving as a guidance point to uniformly distribute the frictional resistance encountered by the conical tip 20 when the tube 11 is inserted into the body cavity (not shown). As shown in FIGS. 1-4 and FIG. 7, the outer diameter of the tube 11 converges smoothly at the distal end portion of the tube defining a truncated cone 20 and the return lumen 13 opens at the truncated apex of the cone 18. Preferably, the conical tip 20 has a gradual taper. The conical tip 20, for example, has a length of at least approximately two diameters of the tube 11. Since the frictional resistance is uniformly distributed and the conical tip 20 smoothly merges with the body of the tube 11, insertion trauma and kinking are minimized.

The relatively small size of the return and inlet apertures 18, 19 further reduce insertion trauma, but they also impede fluid flow. Therefore, an additional group of holes or apertures generally designated 21 connect the return lumen 13 to the outer surface of the tube 11, and an additional group of holes or apertures 22 connect the inlet lumen 14 to the outer surface of the tube 11. Viewed from the side, the holes 21, 22 are seen to have scaphoid margins. In particular the return holes or apertures 21 are axially disposed between the base of the conical tip 20 and the inlet aperture 19 at the distal end of the inlet lumen 14. The additional inlet holes or apertures 22 are axially disposed between the inlet aperture 19 and the proximal end of the tube 11. The return holes 21 and the inlet holes 22 are further disposed circumferentially on opposite sides of the divider 12. Thus, there is axial as well as circumferential separation of the inlets and outlets for fluid circulation.

In accordance with another aspect of the invention specifically shown in FIG. 7, the conical tip generally designated 20 is formed with a relative concentration of material 23 to stiffen the tip 20. This stiffening aids penetration of the tip 20 into the body cavity (not shown) and also aids the dilation of soft tissue such as veins. As shown in FIG. 7, the inlet lumen 14 terminates at the inlet aperture 19 and in place of the inlet lumen the relative concentration of material 23 extends axially from the aperture 19 to the distal end of the tube 11 at the truncated apex of the conical tip 20. Also, the wall thickness of the conical tip 20, the reurn lumen 13 and the aperture 18 are all eccentric to the axis of the conical tip.

It is readily apparent to persons of ordinary skill in the art that the tip 20 as shown in FIG. 7 is easily formed from thermo-plastic material. The tip 20 including the relative concentration of material 23 is easily molded and bonded or is integrally formed from the cylindrical tube 11 by the use of internal and external mandrels and the application of heat by any number of conventional means such as RF forming, thermal forming, or infrared forming.

For use in hemodialysis, the smooth bore double lumen catheter 10 is introduced in the direction of blood flow in a large vein over a hypodemic needle or Seldinger's guide wire, or through a sheath as is conventional. The side holes 19 and 22 on the blood inlet lumen 14 draw the blood for processing and the processed blood is returned through the return lumen 13 and out through the holes 18, 21 to return the blood upstream into circulation. As was described above, the geometrical properties of the smooth bore double lumen catheter as shown in the drawing figures insure that insertion trauma, kinking, and the possibility of clotting are minimized during hemodialysis.

What is claimed is:

1. A double lumen catheter comprising an elongated unitary cylindrical tube having a longitudinal planar septum of one-piece construction with said tube, said septum dividing the interior of said tube into first and second lumens, the proximal end of said cylindrical tube connecting to two separate tubes communicating with the respective first and second lumens for the injection and removal of fluid, the first lumen extending from the proximal end of said cylindrical tube to an opening at the distal end of said cylindrical tube, and the second lumen extending from the proximal end of said cylindrical tube to at least one opening in the side of the cylindrical surface of said cylindrical tube, said opening to said second lumen being axially spaced from the distal end of said cylindrical tube, said cylindrical tube having at its distal end a smooth conical tapered tip that smoothly merges with the cylindrical surface of said cylindrical tube around the entire circumference of said tube, said first lumen and the internal wall thereof formed by said septum extending continuously through said conical tapered tip, and having a uniform diameter along its entire length from its proximal end to said conical tapered tip.

2. The double lumen catheter as claimed in claim 1, wherein the cylindrical surface of said cylindrical tube includes at least one side hole exposing said second lumen that is axially spaced between the opening to said second lumen and the proximal end of said cylindrical tube and is circumferentially disposed on the same side of the cylindrical tube as the opening to said second lumen.

3. The double lumen catheter as claimed in claim 1, wherein said conical tapered tip comprises a concentration of material substantially exceeding the concentration of material in the cylindrical body of said cylindrical tube.

4. The double lumen catheter as claimed in claim 1, wherein said cylindrical tube comprises a relative concentration of material extending axially from said opening in the side of said cylindrical surface of said cylindrical tube to the distal end of said cylindrical tube.

5. The double lumen catheter as claimed in claim 1, wherein said second lumen terminates at said opening in the side of said cylindrical surface of said cylindrical tube, and a relative concentration of material extends axially from said opening in the side of said cylindrical surface of said cylindrical tube to the distal end of said cylindrical tube.

6. The double lumen catheter as claimed in claim 1, wherein the apex of said conical tip is substantially aligned with the axis of said cylindrical tube.

7. The double lumen catheter as claimed in claim 1, wherein the length of said conical tip is at least approximately two diameters of said cylindrical tube.

8. The double lumen catheter as claimed in claim 1, wherein the first and second lumens are semicircular.

9. The double lumen catheter as claimed in claim 1, wherein the proximal end of said cylindrical tube is connected to said separate tubes by a connector including a sleeve coaxial with said cylindrical tube at the junction of the coaxial tube and the connector.

10. A double lumen catheter as claimed in claim 1, wherein the opening at the distal end of said cylindrical tube is eccentric with respect to the axis of the conical tapered tip.

11. The double lumen catheter as claimed in claim 1, wherein the wall thickness of the conical tapered tip is eccentric with respect to the axis of the conical tapered tip.

12. A double lumen catheter comprising an elongated cylindrical tube including a planar axial divider bisecting said cylindrical tube into first and second lumens, the proximal end of said cylindrical tube connecting two separate tubes communicating with the respective first and second lumens for the injection and removal of fluid, the first lumen extending from the proximal end of said cylindrical tube to a first opening at the distal end of said cylindrical tube, the second lumen extending from the proximal end of said cylindrical tube to a second opening in the side of the cylindrical surface of said cylindrical tube, said second lumen terminating at said second opening and a relative concentration of material extending axially from the second opening to the distal end of said cylindrical tube, the distal end of said cylindrical tube having a smooth conical tapered tip that smoothly merges with the cylindrical surface of said cylindrical tube, the cylindrical surface of said cylindrical tube having at least one side hole exposing said first lumen axially spaced between said second opening and said conical tapered tip and circumferentially disposed on the opposite side of said cylindrical tube as said second opening, and the cylindrical surface of said cylindrical tube having at least one side hole exposing said second lumen axially spaced between said second opening and the proximal end of said cylindrical tube and circumferentially disposed on the same side of said cylindrical tube as said second opening.

13. The double lumen catheter as claimed in claim 12, wherein the apex of said conical tip is substantially aligned with the axis of said cylindrical tube.

14. The double lumen catheter as claimed in claim 12, wherein the length of said conical tip is at least approximately two diameters of said cylindrical tube.

15. The double lumen catheter as claimed in claim 12, wherein the first opening in the distal end of said cylindrical tube is eccentric with respect to the axis of the conical tapered tip.

16. The double lumen catheter as claimed in claim 12, wherein the wall thickness of the conical tapered tip is eccentric with respect to the axis of the conical tapered tip.

17. The double lumen catheter as claimed in claim 12, wherein the first and second lumens are semicircular.

18. The double lumen catheter as claimed in claim 12, wherein the proximal end of said cylindrical tube is connected to said separate tubes by a connector including a sleeve coaxial with said cylindrical tube at the junction of the connector and said cylindrical tube.

19. A double lumen catheter comprising an elongated unitary tube including an integral septum extending axially along the entire length of the tube and dividing the interior of said tube into a first and a second lumen, the outer circumference of said tube converging smoothly at the distal end portion of said tube defining a truncated cone, the first lumen opening at the truncated apex of said cone, and the second lumen being shorter in axial length than the first lumen and opening upon the outer circumference of said tube, said tube having a uniform diameter from its distal end portion to proximally beyond the opening of the second lumen upon the outer circumference.

20. The double lumen catheter as claimed in claim 19, wherein the first lumen is eccentric to the axis of said cone.

21. The double lumen catheter as claimed in claim 19, wherein said second lumen opens upon the outer circumference of said tube at a plurality of openings having scaphoid margins.

22. The double lumen catheter as claimed in claim 19, wherein said second lumen opens upon the outer circumference of said tube at a plurality of holes.

23. The double lumen catheter as claimed in claim 19, wherein said first and second lumens are semicircular.

24. The double lumen catheter as claimed in claim 19, further comprising a branching connector at the proximal end of said tube including sleeve coaxial with said tube at the junction of said tube and the branching connector.

25. A double lumen catheter comprising an elongated unitary cylindrical tube having a longitudinal planar septum of one-piece construction with said tube, said septum dividing the interior of the tube into first and second lumens, the proximal end of said cylindrical tube connecting to two separate tubes communicating with the respective first and second lumens for the injection and removal of fluid, the first lumen extending from the proximal end of said cylindrical tube to an opening at the distal end of said cylindrical tube, and the second lumen extending from the proximal end of said cylindrical tube to at least one opening in the side of the cylindrical surface of said cylindrical tube, said opening to said second lumen being axially spaced from the distal end of said cylindrical tube, said cylindrical tube having at its distal end a smooth conical tapered tip that smoothly merges with the cylindrical surface of said cylindrical tube around the entire circumference of said tube, said first lumen and the internal wall thereof formed by said septum extending continuously through said conical tapered tip, and wherein said cylindrical tube comprises a relative concentration of material extending axially from said opening in the side of said cylindrical surface of said cylindrical tube to the distal end of said cylindrical tube.

* * * * *